(12) United States Patent
Ariglio et al.

(10) Patent No.: US 6,359,686 B1
(45) Date of Patent: Mar. 19, 2002

(54) INSPECTION SYSTEM FOR SHEET MATERIAL

(75) Inventors: James A. Ariglio, Painted Post, NY (US); Ted A. Brownlee, Livermore, CA (US); Vincent W. Howell; Jeffrey C. McCreary, both of Horseheads, NY (US); Alan G. Ryder, Big Flats, NY (US); Steven A. Shifman, San Ramon; Peter M. Voit, Dublin, both of CA (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 09/342,285

(22) Filed: Jun. 29, 1999

(51) Int. Cl.[7] .............................................. G01N 21/896

(52) U.S. Cl. .................... 356/239.1; 356/431

(58) Field of Search ................................ 356/429, 430, 356/431, 239.1; 250/559.48

(56) References Cited

U.S. PATENT DOCUMENTS

| | | | | |
|---|---|---|---|---|
| 3,668,955 A | * | 6/1972 | Rupprecht et al. | 83/879 |
| 3,740,524 A | * | 6/1973 | Dahlberg et al. | 219/121.69 |
| 3,754,146 A | * | 8/1973 | Chow | 250/559.48 |
| 3,975,644 A | * | 8/1976 | Scharf | 356/430 |
| 4,274,747 A | * | 6/1981 | Van Beeck et al. | 356/431 |
| 4,619,681 A | * | 10/1986 | Tetaz et al. | 356/239.1 |
| 5,246,331 A | * | 9/1993 | Hallahan et al. | 414/676 |

* cited by examiner

Primary Examiner—Richard A. Rosenberger
(74) Attorney, Agent, or Firm—Maurice M. Klee

(57) ABSTRACT

An inspection system is set forth for the inspection of surface and body defects within glass substrates. The glass is supported by an inclined air table during the inspection process to provide planar stability and minimize vibration. The sheet is indexed a given distance along an oblique axis parallel to the air table and stopped, wherein a scanning mechanism having portions on opposite sides of the air table moves transversely of the sheet in alignment with slots formed in the air table, and the process is repeated until the sheet is completely scanned.

14 Claims, 6 Drawing Sheets

INSPECTION SYSTEM FOR SHEET MATERIAL

BACKGROUND OF THE INVENTION

The invention relates to an inspection system for the inspection of defects in sheet material, and more particularly to an inspection system for the inspection of surface and body defects in glass substrates, such as in LCD glass. The inspection system is particularly adapted to accommodating fairly large size substrates in the order of 550 mm×650 mm and larger, by providing stability to the substrate during inspection through the use of an air support table.

Presently, the inspection of such large size glass panels is primarily done by utilizing manual methods. Accordingly, such manual processes introduce a large amount of variability in the outgoing inspection product. Some of the problems encountered with the known inspection systems include the problem of holding a substrate in a manner which minimizes sheet vibration. In addition there has been problems in holding the glass sheet in a strict plane tolerance so as to have consistency in inspection readings. Further, it has been difficult to provide a direct view of all areas of the sheet without interference from supporting structures. That is, most of the known inspection systems rely on some method of holding the sheet by the edge in either a horizontal or vertical orientation, which creates problems of glass sag and vibration during the inspection process.

It thus has been an object of the present invention to provide a solution to these problems by utilizing a uniform air support for the entire glass surface of a substrate without physically contacting the surface of the sheet, and while dampening any sheet vibrations and allowing the sheet to move at high speeds during inspection.

SUMMARY OF THE INVENTION

The present invention sets forth method and apparatus for inspecting surface and body defects in glass substrates. The system includes a dual detector scanning system as well as a brightfield/darkfield imaging system that work together to detect, identify and classify different types of glass defects. The glass is supported in a slightly off-vertical position by an air table during the inspection process to provide stability, particularly for larger size substrates in the order of 550 mm×650 mm and larger.

Glass sheets or substrates to be inspected are positioned adjacent a three-piece air table which is tilted by an angle from the vertical. The sheets or substrates are indexed substantially vertically, but along an incline or axis parallel to the tilted air table. Dual light delivery mechanisms and dual detectors are positioned adjacent slots formed within the air table on a slide mechanism that allows them to be moved horizontally along an axis transverse to the oblique axis. The glass substrate is positioned over the slots and held stationary while the dual detector and light delivery systems are swept from one edge of the substrate to the other. The glass is then indexed and this process is repeated until the entire area of the glass substrate has been inspected.

Following this initial inspection process, brightfield/darkfield optics can be positioned to review any of the particles or defects detected during the previous scanning process. Scratches, particles and other defects can be identified and accepted or rejected.

DESCRIPTION OF THE PREFERRED EMBODIMENTS

Figure 1:
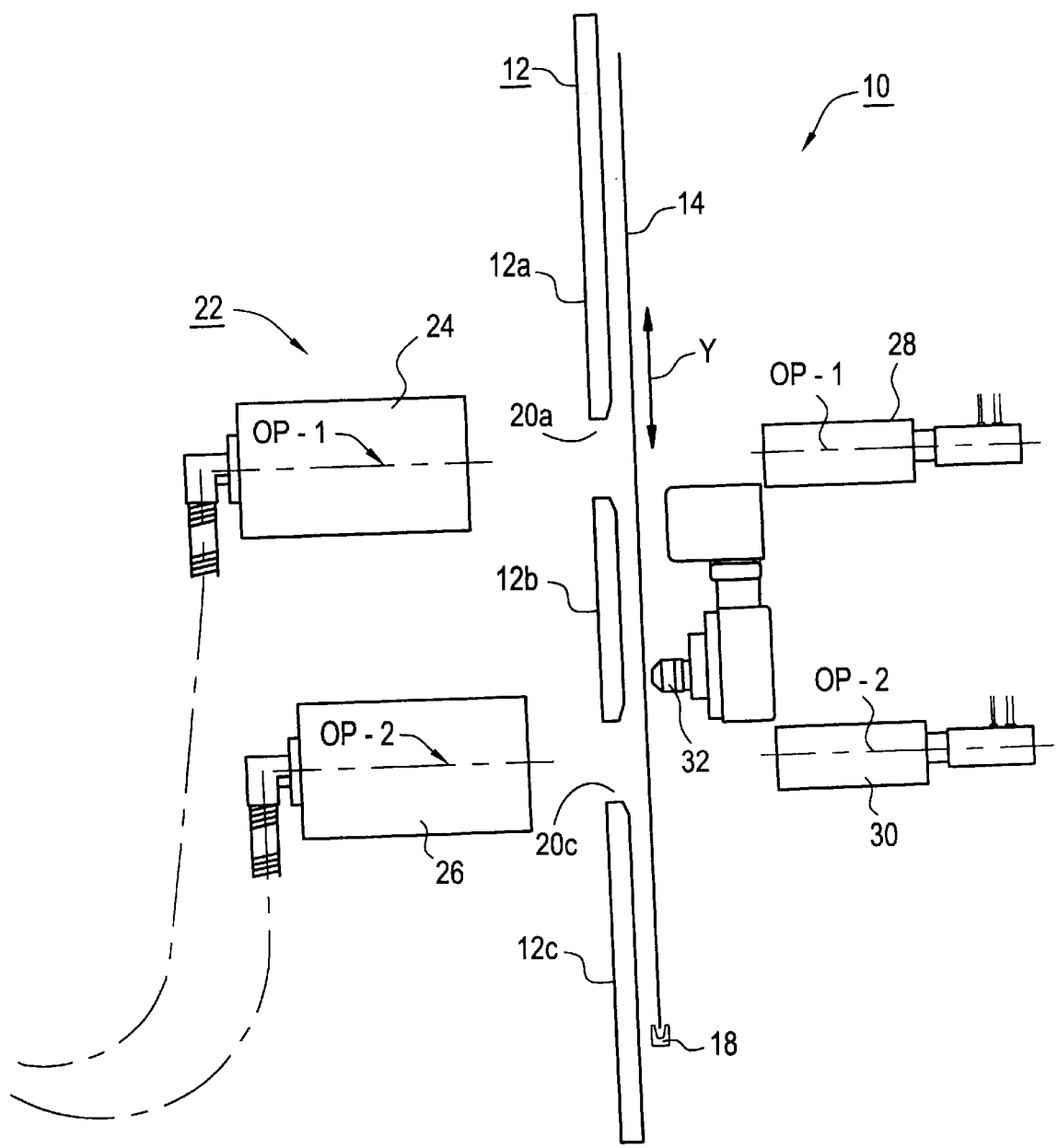
FIG. 1 is a schematic side elevational view of an inspection system embodying the present invention.

Referring now to FIG. 1, the scanning portion of an inspection system 10 is schematically shown in elevation. An inclined air table 12 formed in three sections, including upper section 12a, middle section 12b, and lower section 12c, preferably is positioned at an angle to the vertical. A specimen to be examined such as a glass sheet or substrate 14 is supported at its bottom edge 16 by a pair of groove finger supports 18 (see also FIG. 2 and FIG. 3). The glass specimen or substrate 14 to be examined or inspected, is maintained parallel to the inclined plane of the air table 12 by means of an air cushion supplied by the air table. As will be explained in more detail hereinafter, the substrate 14 is moved upwardly and downwardly along an oblique Y axis, shown by arrow Y, which is parallel to the plane of the air table 12 and at a desired acute angle from a true vertical.

As shown, the air table 12 has gaps or slots 20a and 20c formed between middle section 12b and its associated first and second sections 12a, 12c, respectively. The scanning mechanism 22 of the inspection system 12 is positioned on opposite sides of the glass substrate 14 adjacent the gaps or slots 20a, 20c. The scanning mechanism includes first and second light delivery systems 24, 26, and an optically aligned dual detector system, for example a dual camera system, including first detector 28 and second detector 30. The light delivery systems 24, 26 are positioned on one side of the air table 12, and the first detector 28 and second detector 30 of the dual detector system are positioned on the opposite side of the table 12. However, the first light delivery system and the first detector are in optical alignment along optical axis OP-1 through slot or gap 20a, whereas the second light delivery system 26 and the second camera 30 are in optical alignment along optical axis OP-2 through the lower slot or gap 20c. The scanning mechanism 22 moves in unison along a horizontal X axis (shown by arrow X in FIG. 4) transversely of the glass substrate 14 and the Y axis, as more particularly set forth hereinafter with respect to FIG. 4 and FIG. 5. The scanning mechanism 22 also includes a third detector 32, for example, a camera with brightfield/darkfield optics, which is utilized after the initial scanning by the dual detector system to further classify a defect initially located by the dual detector system. The third detector preferably has a higher resolution than the first and second detectors.

Figure 2:
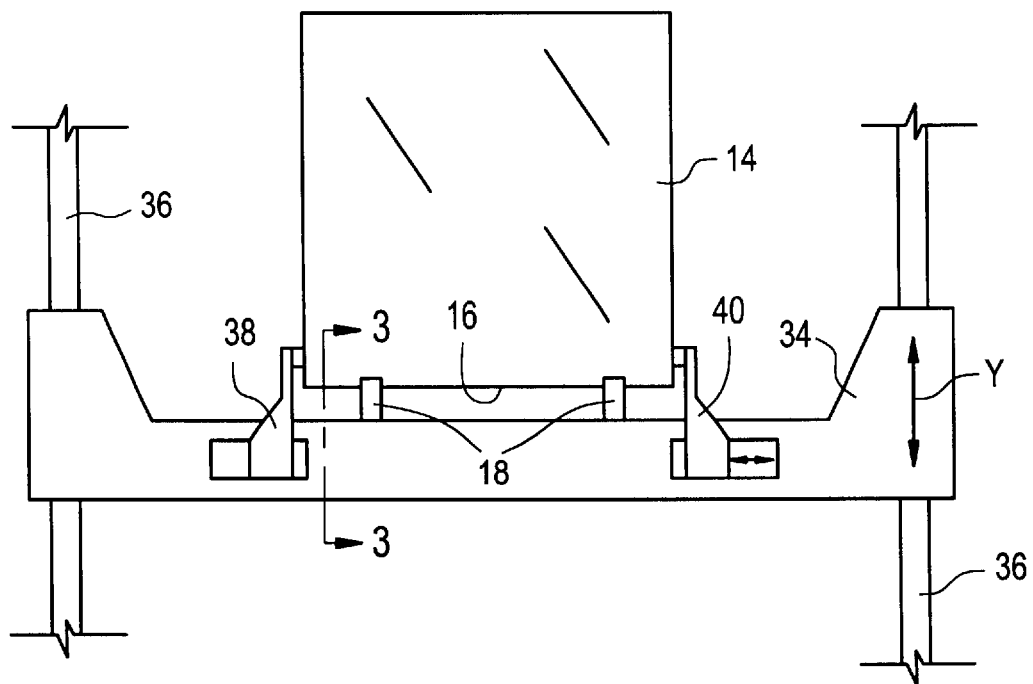
FIG. 2 is a schematic front elevational view of the mechanism for receiving and vertically indexing the glass substrate.
Figure 3:
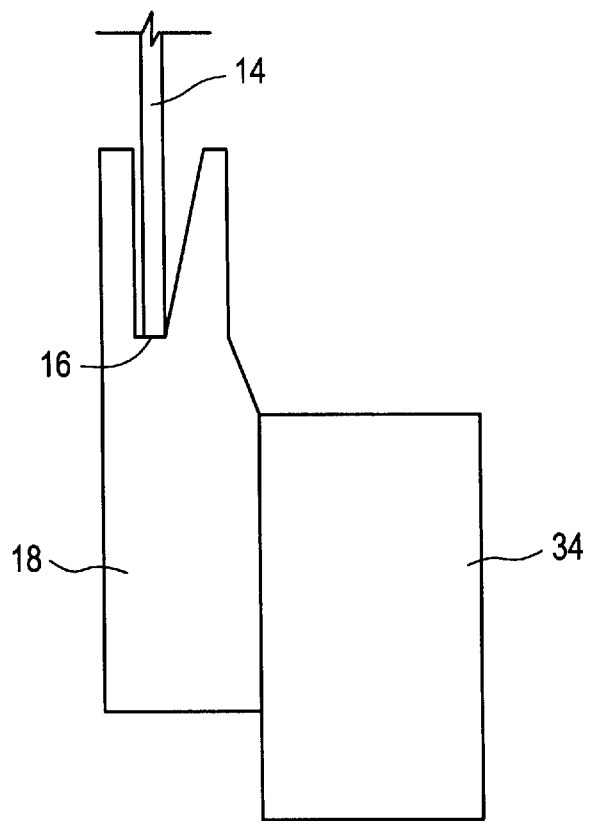
FIG. 3 is a fragmental schematic illustration taken along lines 3—3 of FIG. 2 illustrating the V-groove finger for supporting the bottom edge of the glass substrate.
Figure 4:
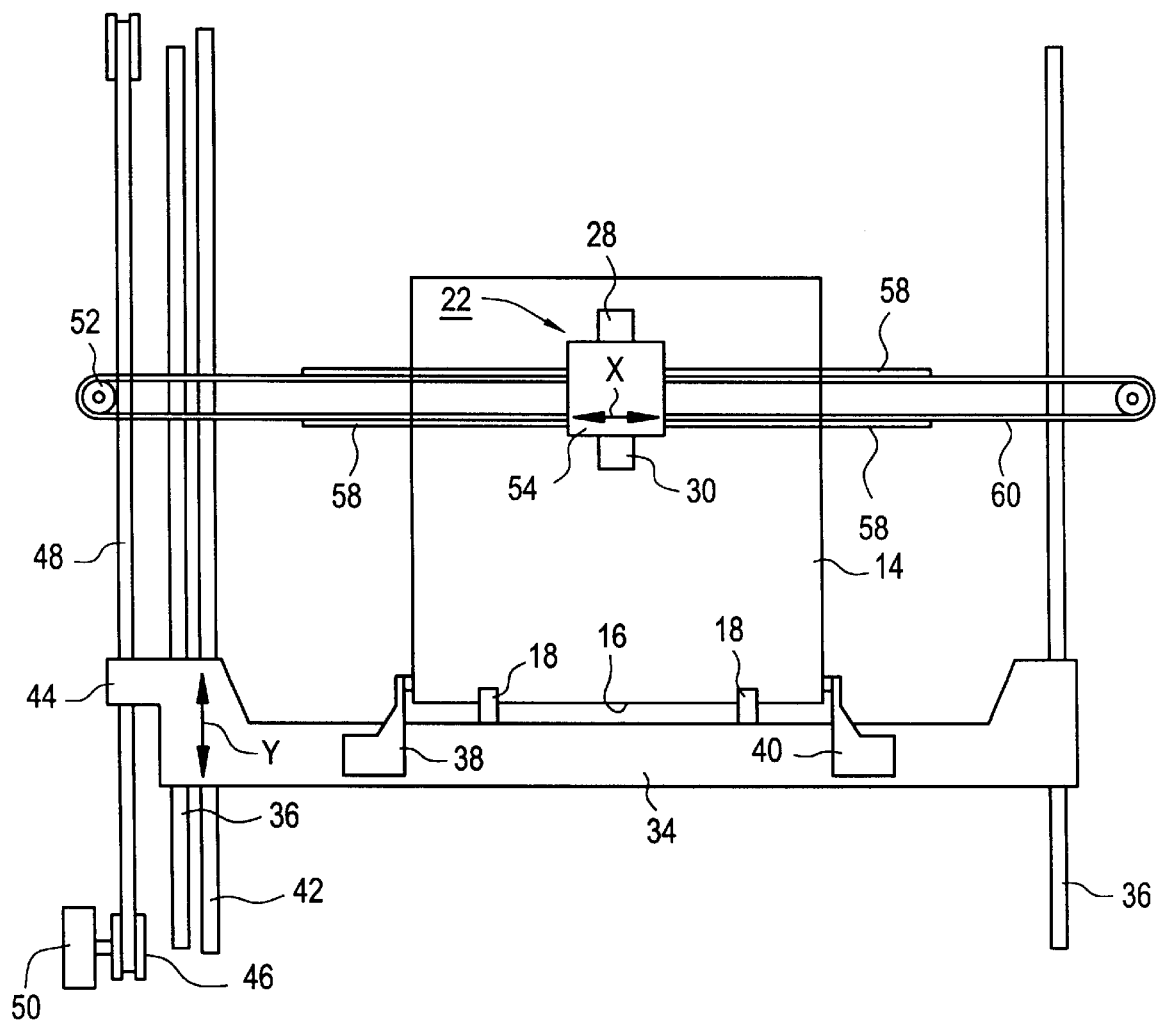
FIG. 4 is a schematic front elevational view illustrating the mechanism for vertically indexing at an angle parallel to that of the air support table, and the mechanism for horizontally sweeping the light delivery mechanisms and cameras.

Referring now to FIGS. 2, 3 and 4, it can be seen that the grooved finger supports 18 are secured to a carriage plate 34 which is moveable along the oblique Y axis by means of guide rails 36. A pair of centering pads 38, 40 are also secured to the carriage plate 34. The left centering pad 38 functions as a positioning pad to accommodate different sizes of glass substrates 14 and may be placed in a desired position by means of an actuator, for example, a rotary pneumatic actuator.

Referring now more particularly to FIG. 4, both the glass substrate transport mechanism for moving the glass substrate upwardly and downwardly along the oblique Y axis parallel to the air table 12, and the scanning mechanism 22 for moving the light delivery systems and the dual detector system horizontally along the X axis are driven by motors, for example linear motors through a timing belt, pulley and guide arm system. The glass substrate transport assembly, which includes the finger supports 18, the carriage plate 34, guide rails 36 and the centering pads 38, 40 is driven by a linear motor 42 through drive pulley 46 and timing belt 48 connected to an arm 44 of the carriage plate 34. A brake 50, connected to the drive pulley 46 is provided to prevent the carriage plate 34 from falling along the Y axis when power is lost to the linear motor 42. A separate linear motor (not shown) is similarly connected to the drive pulley 52 and drive shaft 52a for operating the scanning mechanism 22.

Figure 5:
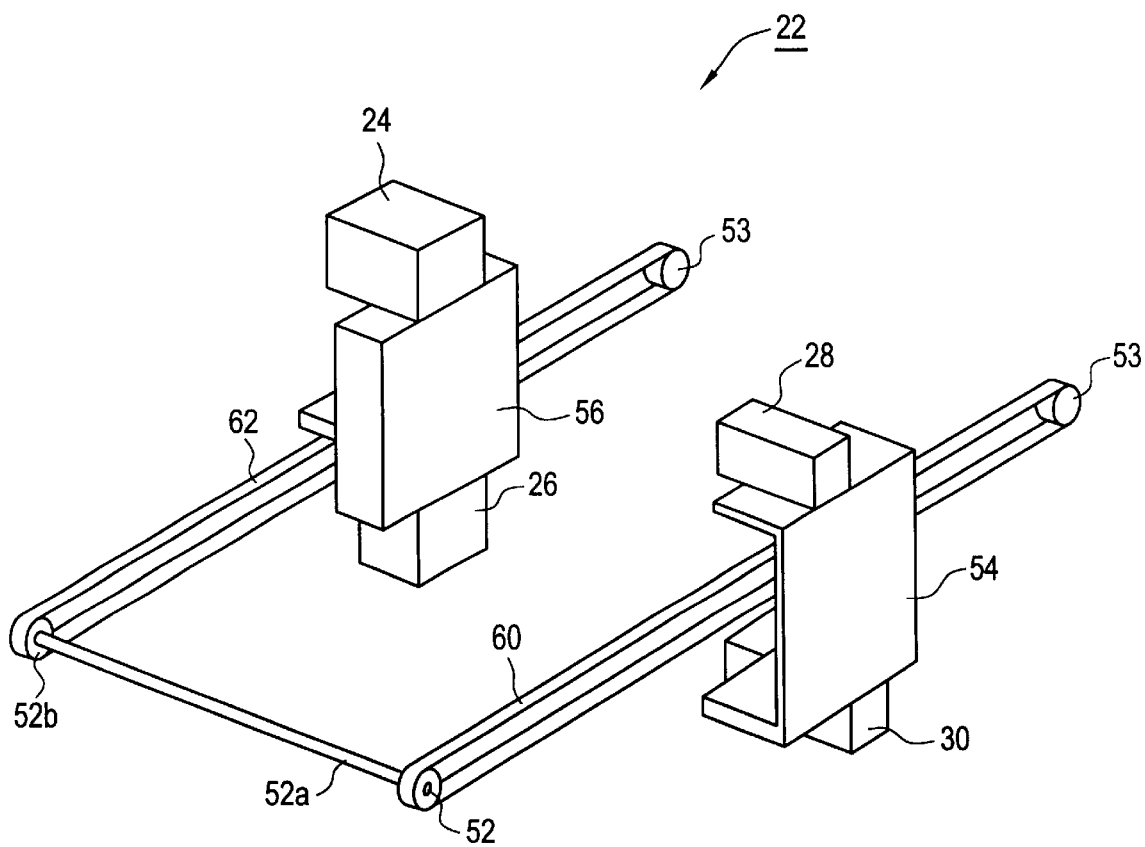
FIG. 5 is a perspective schematic representation further illustrating the mechanism for horizontally moving the light delivery systems and the cameras in unison.

Referring now more particularly to both FIG. 4 and FIG. 5, the horizontal movement of the scanning mechanism 22 transversely of the glass substrate 14 can be seen. The scanning mechanism 22 is positioned on opposite sides of the glass substrate transport assembly, which assembly moves the glass substrate 14 substantially vertically along the Y axis. The first detector 28 and the second detector 30 are supported by a detector mount 54, whereas the first light delivery system 24 and the second light delivery system 26 are supported by a lighting system mount 56. The mounts 54, 56 slide transversely of the sheet 14 along the X axis on rails 58, such as shown in FIG. 4 for the camera mount 54. A pair of timing belts 60, 62 are connected to the detector mount 54 and the lighting system mount 56, respectively, for moving the light delivery systems and the detectors in unison along the X axis. The linear motor driving drive pulley 52 and timing belt 60 for moving the cameras along the X axis, also drives the lighting systems along the X axis through a connecting drive shaft 52a and drive pulley 52b which operates timing belt 62. A pair of idler pulleys 53 at the opposite ends of the timing belts 60, 62 maintain the belts in tension.

Figure 6:
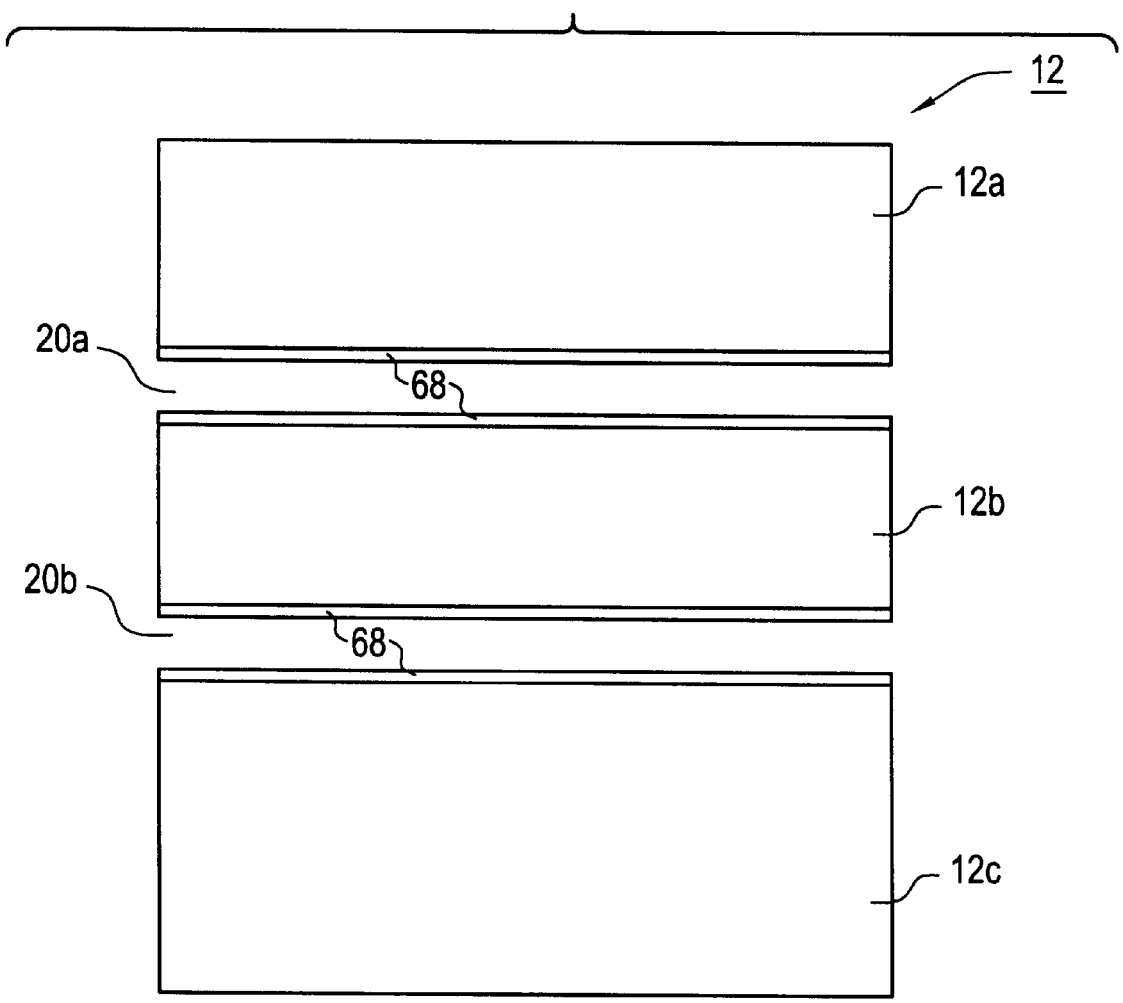
FIG. 6 is a schematic elevational view of the sections of the air table.
Figure 7:
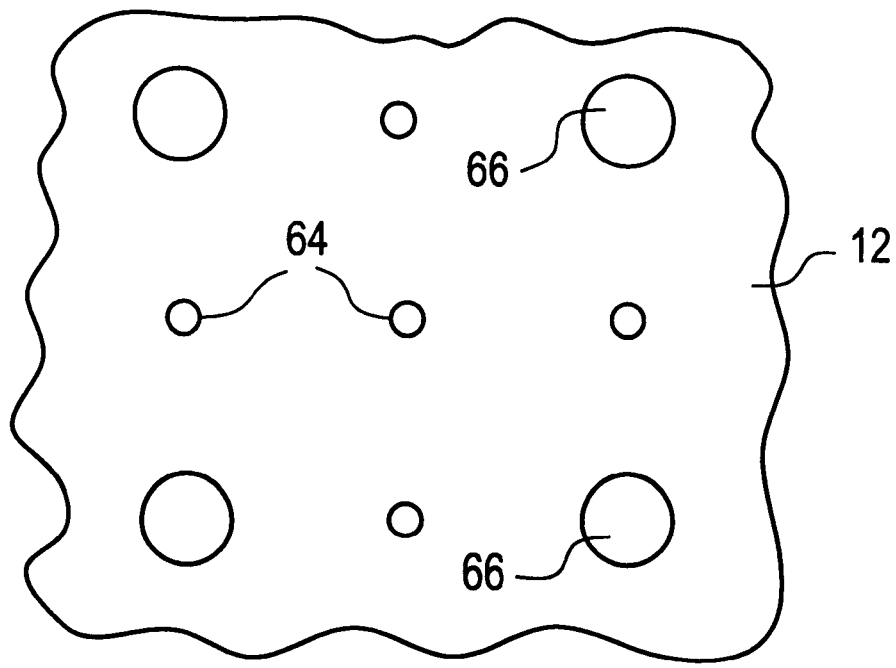
FIG. 7 is an enlarged schematic fragmental view of a section of the air table illustrating an air hole pattern.

Referring now to FIGS. 6 and 7, the air table and its hole patterns are shown in more detail. The air table 12 with its upper section 12a, middle section 12b, lower section 12c and gaps 20a and 20c is shown in FIG. 6, whereas air supply holes 64 and air exhaust holes 66 are shown in a portion of the table 12 in FIG. 7. The hole pattern for the air table is specifically designed to provide the required float of the glass sheet 14 off of the table, as well as maintaining flatness of the sheet. In view of the fact that edge portions of the glass sheet will lose or exhaust more air from the sheet surface than centrally of the sheet, exhaust holes are provided centrally of the sheet in order to provide uniform air flow against the surface of the sheet and prevent bowing of the sheet in the center portion thereof. Thus, the flatness of the sheet is provided through a pattern of pressure and exhaust holes, with the exhaust holes being sized, with respect to their location on the table to thereby maintain even pressure to the back of the sheet across the full surface thereof. As noted particularly in FIG. 6, there is a tapered gap interface 68 adjacent the gap 20a and the gap 20b. Each of the gap interfaces is provided with additional air supply holes 64 to compensate for the loss of pressure adjacent the gaps 20a and 20b.

As previously mentioned, the inclined air table 12 is tilted at an angle to the vertical so that it is parallel to the oblique Y axis. Preferably the acute angle should be between about 5° and 15° from the vertical. If the angle is much less than 5° from the vertical, the pressure necessary to maintain the glass sheet in a flowing position off of the table must be very carefully controlled, since if too much pressure is applied the sheet will be blown off of the table. Although angles greater than 15° may be utilized, the closer the angle comes to 90°, and the glass sheet is virtually horizontal, the greater are the problems encountered with regard to sagging. Although by no means limiting, an angle of 7½° from the vertical does provide excellent results.

Figure 8:
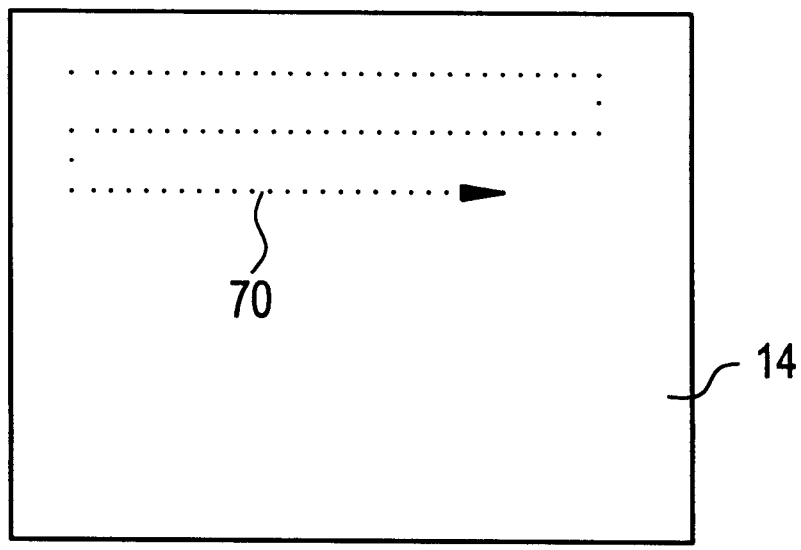
FIG. 8 is a schematic illustration of what an actual scanning pattern would look like on the glass sheet.

In operation, a glass sheet or substrate 14 is positioned with its bottom edge 14 within grooved finger supports 18 on carriage plate 34. The centering pads 38 and 40 are utilized to center the sheet 14 on the carriage plate 34. The left centering pad 38 is actuated by a cam action to position the pad in a fixed position relative to the size of the sheet being utilized, and the right centering pad 40 is spring actuated to allow the glass to center. Air is supplied to the air supply holes 64 of the inclined air table 12 so as to position an support the glass sheet 14 along a desired inclined or oblique Y axis which is parallel to the air table 12. Linear motor 42, through drive pulley 46 and timing belt 48, moves the carriage plate 34 along guide rails 36 so as to move the glass sheet 14 along the Y axis parallel to air table 12. The glass sheet 14 is moved along the Y axis a predetermined distance and is then held in position by the linear motor. The linear motor driving the X axis is then actuated so as to sweep the scanning mechanism 22 across the width of the glass. When the sweep of the scanning mechanism is completed, the glass is moved along the Y axis another predetermined distance so that the detector and optics of the scanning mechanism can make another pass across the glass. This procedure is repeated until the entire sheet of glass has been scanned. The glass may be moved in either an upwardly or downwardly movement during the scanning, and an actual pattern is shown in FIG. 8 when the glass is moved in an upward position. Although the trace 70 of the scanning pattern is shown as a line, the actual field of view of the cameras cover the entire surface between the parallel trace lines. With commercially available optics, a movement along the Y axis of about 1.5 cm between sweeps of the scanning mechanism provides complete coverage of the sheet. The motion along the X and Y axes is controlled by motion control electronics.

Following the initial scanning of the sheet, a more detailed scan of the sheet then is effected. Brightfield/darkfield optics are then positioned to further review any of the particles or defects detected during the initial scanning process. To locate a particular X, Y coordinate, the glass is moved vertically a Y distance along the Y axis and the detectors are moved horizontally an X distance along the X axis. The optics of the third detector 32 have a higher magnification than the initial scanning detectors so that the system can find out which surface the particle is on, its size, and also display an image of the particle so it can be further characterized. As will be appreciated by those skilled in the art, algorithms known in the art can be utilized to identify and characterize defects such as scratches and particles in the sheet of material being scanned. Those skilled in the art will appreciate that the algorithm used to accept or reject a defect will be determined by the material being scanned, as well as the acceptable size of the defect for a particular application.

Although we have disclosed the now preferred embodiments of the invention, it will be apparent to those skilled in the art that various changes and modifications may be made thereto without departing from the spirit and scope of the invention as set forth in the appended claims.

What is claimed is:

1. Apparatus for inspecting sheet material comprising:
   an inclined air table positioned in a plane parallel to a first axis which lies at an angle to the vertical,
   means for moving said sheet material along said first axis and parallel to said air table and physically supporting said sheet material solely along bottom edge portions of said sheet,
   air supply means for supporting said sheet material parallel to, and at a desired distance from, said air table so as to avoid physical contact with surface portions of said sheet,
   scanning means, and
   means for moving said scanning means along a second axis which lies transversely across at least one surface of said sheet material.

2. Apparatus for inspecting sheet material as defined in claim 1 wherein said inclined air table has a first slot and a second slot formed across the surface thereof parallel with said second axis.

3. Apparatus for inspecting sheet material as defined in claim 2 wherein said scanning means includes a first detector and a first light source in alignment with the first slot, and a second detector and second light source in alignment with the second slot.

4. Apparatus for inspecting sheet material as defined in claim 1 wherein said air table is provided with an air supply hole pattern to supply air pressure to the sheet material, and an air exhaust hole pattern for selectively exhausting the supplied air so as to maintain the sheet substantially parallel with the air table.

5. Apparatus for inspecting sheet material as defined in claim 1 wherein said means for physically supporting bottom edge portions of said sheet includes means for centering said sheet on said support means.

6. Apparatus for inspecting sheet material as defined in claim 1 wherein said inclined air table has open portions formed transversely across surface portions thereof, said sheet material is transparent, and wherein said scanning means includes a first light delivery system and first camera positioned on opposite sides of said air table and in alignment with one of said open portions formed therein, and a second light delivery system and a second camera also positioned on opposite sides of said air table and in alignment with another of said open portions formed therein.

7. Apparatus for inspecting sheet material as defined in claim 1 including brightfield/darkfield optic means forming a part of said scanning means for reviewing any defects detected during the scanning of said sheet.

8. A method of inspecting sheet material which comprises:
   supporting a sheet of material to be inspected along an inclined axis by means of air pressure,
   periodically moving said sheet of material a predetermined distance along said inclined axis, and
   scanning at least one surface of said sheet material along an axis transverse to said inclined axis.

9. A method of inspecting sheet material as defined in claim 8 including the step of physically supporting the sheet of material solely along bottom edge portions of the sheet.

10. A method of inspecting sheet material as defined in claim 8 including the steps of providing an air table having a plurality of slots extending transversely across at least a portion of the table, positioning the air table parallel to the inclined axis, and supplying air pressure through the air table to support the sheet material along the inclined axis parallel to the air table.

11. A method of inspecting sheet material as defined in claim 10 including the steps of providing a glass sheet to be inspected, providing at least one light source on one side of said air table, providing at least one detector on an opposite side of said table, aligning at least one light source and at least one detector with one of the plurality of slots in said air table, and moving said aligned light source and detector transversely across the sheet supported by said air table and thereby scanning and inspecting said sheet for defects.

12. A method of inspecting sheet material as defined in claim 8 including the steps of providing brightfield/darkfield optics having higher magnification than that used during scanning, and locating and identifying defects found during scanning.

13. An improved method for inspecting and locating surface and body defects in glass substrates which comprises:
   providing a glass sheet to be inspected,
   positioning an air table, having at least two parallel slots extending transversely across at least a portion of the table, at a desired angle oblique to the vertical,
   supplying air pressure to the air table to support the glass sheet along an inclined axis that is parallel to the air table,
   moving said glass sheet at periodic intervals along said inclined axis,
   providing a pair of light sources on one side of said air table and a pair of detectors on an opposite side thereof,
   aligning each light source with a detector such that one light source and detector are aligned with one of the parallel slots, and the other light source and detector set are aligned with the other slot, and
   moving both aligned light source and detector sets transversely across the glass sheet, between the periodic movement of said glass sheet, and thereby inspecting the sheet for defects.

14. An improved method for inspecting and locating surface and body defects in glass substrates as defined in claim 13 including the step of utilizing brightfield/darkfield optics to identify defects found during the inspecting of the sheet.

* * * * *

UNITED STATES PATENT AND TRADEMARK OFFICE
CERTIFICATE OF CORRECTION

PATENT NO. : 6,359,686 B1
DATED : March 19, 2002
INVENTOR(S) : Ariglio James A. et al.

It is certified that error appears in the above-identified patent and that said Letters Patent is hereby corrected as shown below:

Title page,
Item [56], References Cited, U.S. PATENT DOCUMENTS, insert the following:
-- 4,323,785    4/1982        McComb et al.
   5,078,775    1/1992        Maltby Jr., et al.
   5,969,810    10/1999       Nicks et al. --
FOREIGN PATENT DOCUMENTS, insert the following:
-- EP060160         5/1985
   EP487402         5/1992
   JP01197336       8/1989
   DE4035168 A1     5/1992 --

Signed and Sealed this

Twenty-eighth Day of December, 2004

JON W. DUDAS
*Director of the United States Patent and Trademark Office*